United States Patent [19]

Trembly et al.

[11] Patent Number: 4,881,543

[45] Date of Patent: Nov. 21, 1989

[54] COMBINED MICROWAVE HEATING AND SURFACE COOLING OF THE CORNEA

[75] Inventors: B. Stuart Trembly, Hanover, N.H.; Ralph E. Crump, Turnbull, Conn.

[73] Assignee: Massachusetts Institute of Technology, Cambridge, Mass.

[21] Appl. No.: 212,506

[22] Filed: Jun. 28, 1988

[51] Int. Cl.⁴ .................. A61B 17/36; A61N 5/02
[52] U.S. Cl. .................. 128/303.1; 128/804
[58] Field of Search ........... 128/303.1, 303.13, 804, 128/400, 793

[56] References Cited

U.S. PATENT DOCUMENTS

| | | |
|---|---|---|
| 603,815 | 5/1898 | Duke . |
| 1,108,686 | 8/1914 | Bonis . |
| 1,364,148 | 1/1921 | Springer . |
| 2,126,070 | 8/1938 | Wappler .......................... 128/172.1 |
| 2,347,915 | 5/1944 | Landaoer ........................ 128/370 |
| 2,525,381 | 10/1950 | Tower ............................. 128/172.1 |
| 3,237,623 | 3/1966 | Gordon ........................... 128/24 |
| 3,307,533 | 3/1967 | Liebner .......................... 128/400 |
| 3,948,269 | 4/1976 | Zimmer .......................... 128/303.1 |
| 3,978,864 | 9/1976 | Smith et al. .................... 128/404 |
| 3,991,770 | 11/1976 | LeVeen ........................... 128/413 |
| 4,003,383 | 1/1977 | Bruck ............................. 128/404 |
| 4,014,333 | 3/1977 | McIntyre ........................ 128/240 |
| 4,030,480 | 6/1977 | Meyer ............................ 128/303.1 |
| 4,140,130 | 2/1979 | Storm ............................ 128/404 |
| 4,326,529 | 4/1982 | Doss et al. .................... 128/303 |
| 4,381,007 | 4/1983 | Doss .............................. 128/303.1 |
| 4,528,991 | 7/1985 | Dittmar et al. ................ 128/804 |

OTHER PUBLICATIONS

J. V. Aquavella, *Opthalmic Surgery*, vol. 5, No. 1, Spring 1974, pp. 39–47.
J. D. Doss and J. I. Albillar, *Contact Lens*, Vol. 6, No. 1, Jan.–Mar., 1980, pp. 13–17.
M. L. Swicord and C. C. David, *IEEE Trans. MIT*, Vol. 29, No. 11, Nov., 1981, pp. 1202–1209.
J. D. Doss et al., Los Alamos Scientific Laboratory (Informal Report No. LA-7155-MS), Feb., 1978.
J. J. Rowsey, *Contact & Intraocular Lens Medical Journal*, Vol. 6, No. 1, Jan.–Mar., 1980, 1–12.
J. V. Aquavella et al., *Arch. Ophthalmol.*, Vol. 94, Dec., 1976, pp. 2082–2085.
A. R. Gasset and H. E. Kaufman, *American Journal of Opthalmology*, Vol. 79, No. 2, Feb., 1975, pp. 226–232.
R. H. Keates and Jack Dingle, *Ophthalmic Surgery*, Vol. 6, No. 3, Fall, 1975, pp. 89–92.
E. L. Shaw and A. R. Gasset, *Investigative Ophthalmology*, March, 1975, pp. 181–186.
J. Scheiblich and O. Petrowicz, *Journal of Microwave Power*, 17(3): pp. 203–209 (1982).
K. A. Kues et al., *Bioelectromagnetics* 6: pp. 177–188 (1985).
R. L. McCally et al., *Johns Hopkins APL Technical Digest*, vol. 7, No. 1, pp. 73–91 (1986).
B. S. Trembly and R. H. Keates, "Combined Microwave Heating and Surface Cooling of the Cornea" (Submitted to *IEEE Trans. on Biomed., Eng.*, Dec. 14, 1987).
K. T. S. Yao, *The Journal of Heredity*, 69:409–412 (1978).
J. W. Stronbehn et al., "Comparison of Three Interstitial Hyperthermia Modalities for Cancer Therapy", BEMS, Seventh Annual Meeting Abstracts, June 16–20 (1985), H-7, p. 36.

*Primary Examiner*—Lee S. Cohen
*Attorney, Agent, or Firm*—Hamilton, Brook, Smith & Reynolds

[57] ABSTRACT

A non-invasive method and apparatus of reshaping the cornea to correct hyperopia, keratoconus, or myopia is described. The central stroma of the cornea is heated by microwave electromagnetic energy to the shrinkage temperature of collagen. The microwave applicator for heating stroma comprises an open-ended, coaxial antenna driven at 2450 MHz with apparatus for surface cooling of the cornea by flow of saline transverse to the antenna axis.

16 Claims, 9 Drawing Sheets

FROM
SWEEP OSCILLATOR
12

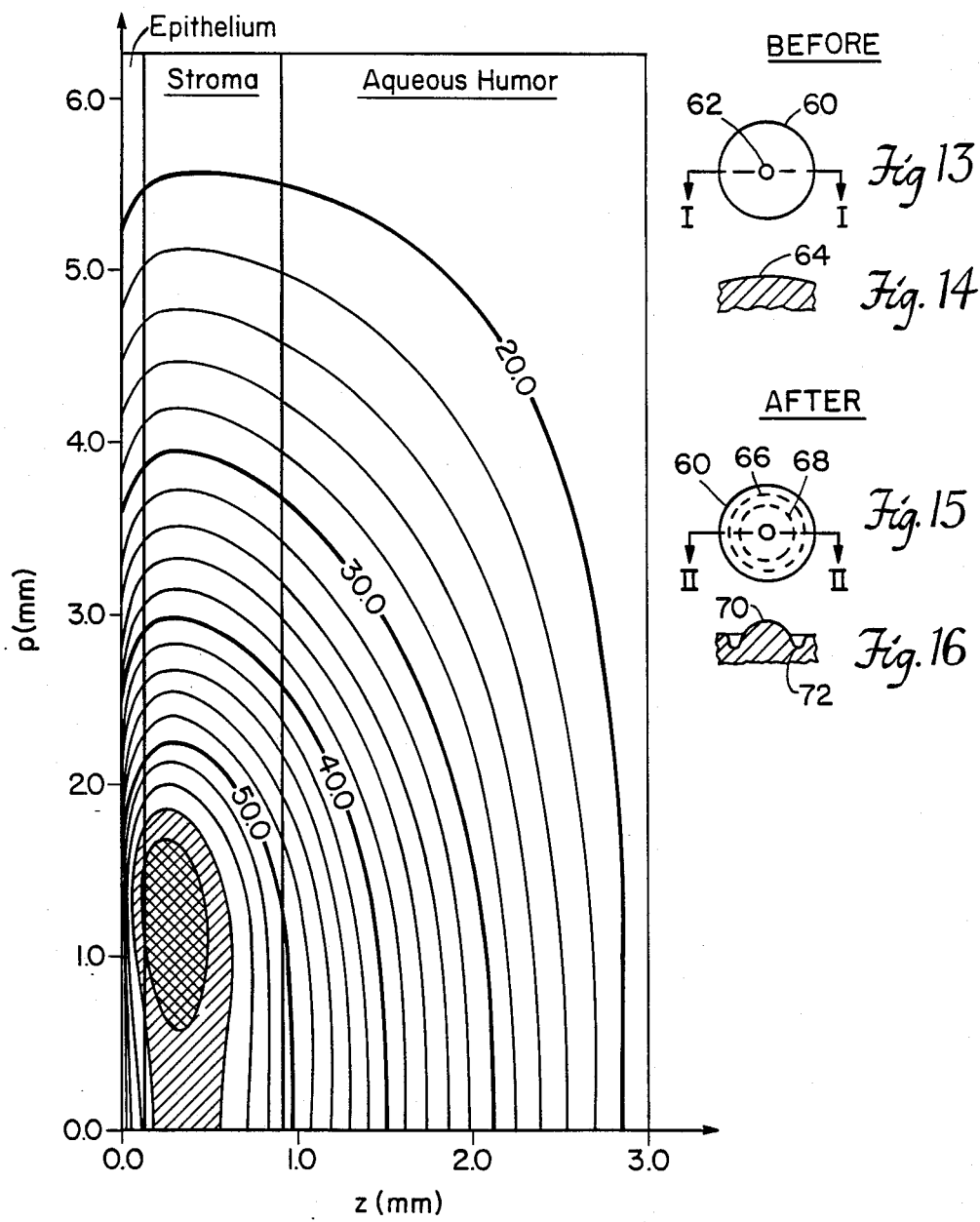
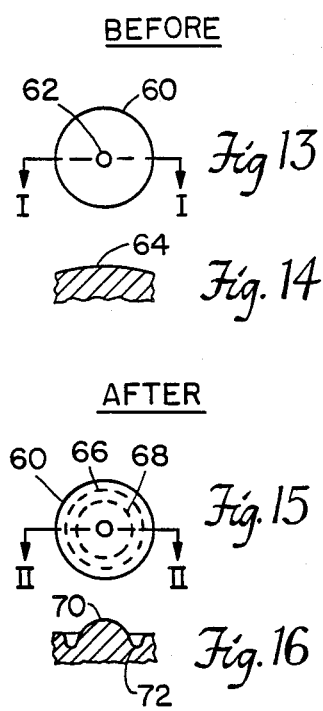
Fig. 12
Fig. 13
Fig. 14
Fig. 15
Fig. 16

COMBINED MICROWAVE HEATING AND SURFACE COOLING OF THE CORNEA

BACKGROUND OF THE INVENTION

For many years, it has been possible to change the shape of the cornea to correct disorders, such as myopia, keratoconus, and hyperopia. In myopia, the dioptric power of the eye is too great; this can be corrected by flattening the cornea. In keratoconus, the cornea has an abnormal cone-shaped projection at its center; it can also be corrected by flattening. Hyperopia can be corrected by increasing the curvature of the cornea to decrease the dioptric power of the eye.

Radial keratotomy is a surgical procedure that can correct myopia by flattening the center portion. Up to sixteen non-penetrating incisions are made in the cornea from near the center outward toward the rim. The internal pressure of the eye causes the cornea to bulge where cuts have been made; the uncut center of the cornea flattens as a result. The side effects of radial keratotomy include perforation of the cornea, glare, and loss of endothelial cells leading to hydration of the cornea.

Because of these drastic side effects, researchers have turned to other techniques for modifying the cornea. One particular approach involves the application of heat to the cornea. Thermal techniques for reshaping the cornea are based on the fact that the cornea stroma shrinks permanently when raised to 55°–58° C. The stroma is the central, thickest layer of the cornea and consists mainly of collagen fibers. If the pattern of shrinkage in the stroma is properly chosen, the resulting stresses can be used to reshape the cornea. The cornea has been flattened to correct keratoconus by applying a heated rod to it (J. V. Aquavella, "Thermokeratoplasty", *Opthalmic Surgery*, Vol. 5, No. 1, Spring 1974, pp 39–47). Since the rod heats by conduction, the maximum temperature occurs at the cornea surface. Thus, the epithelium —the outer layer—can be destroyed. In another thermal approach, the corneal stroma of excised eyes has been heated by radio-frequency techniques combined with surface cooling (J. D. Doss and J. I. Albillar, "A Technique for the Selective Heating of Corneal Stroma", *Contact Lens*, Vol. 6, No. 1, Jan.—Mar. 1980, pp 13–17; U.S. Pat. No. 4,326,529 issued 4/27/82 to James D. Doss). This produces a local maximum of temperature below the epithelium. However, the Doss system requires two conductors, or electrodes, between which the RF current flows. One conductor, i.e., the Rear of Head Electrode of FIG. 5, is a ground-plane. In practice, it must somehow be located behind the eyeball. Therefore, unless the rear electrode is implanted, RF energy must pass completely through the head with possible damaging consequences to eye tissue or other tissue located behind the cornea.

SUMMARY OF THE INVENTION

In the present invention, a microwave heating applicator, which radiates energy a predetermined depth into the cornea, is combined with a surface cooling device to produce a safe and reliable system and process for cornea heat treatment to correct for hyperopia, keratoconus or myopia. The applicator consists of a radiating element of small dimensions. The cornea stroma of the eye can be heated with this one element located a small distance from the cornea surface. The antenna element is dimensioned and spaced from the surface of the eye to establish a known maximum penetration depth of the radiated microwave energy which tapers off to the known depth of the stroma and virtually no further.

The applicator consists of an antenna section and a cooling section. The antenna section has a connector for coupling the antenna to a coaxial cable coupled to a sweep oscillator supplying the microwave energy. The main body of the antenna section is a semi-rigid coaxial cable with inner and outer conductors separated by an insulator. At the applicator, or distal, end of the antenna, a cylindrical stand-off member is coaxially secured to the antenna body or cable by a set screw, which permits the cable to be adjustably translated with respect to the stand-off member.

The stand-off member is formed of a machinable plastic, or other suitable material, such as, stainless steel, and is milled at the distal end to provide wedge-shaped stand-off fingers with at least one channel therebetween transversing the longitudinal axis to permit transverse flow of coolant through the channels. Cornea retention means, in the form of threads, extend across the wedge fingers transversing the longitudinal tube axis to prevent the cornea from excessive bulging when the applicator is applied thereto.

The cooling section is comprised of a curved plastic or metallic applicator tube. One end of the tube is coupled to a pump fed from a saline coolant reservoir. The other end is coupled to a waste container. An eye-conforming arcuate opening is provided on the tube by removing a section of the cylindrical tube along a sidewall near one end of the tube. A transverse bore or opening for insertion of the cylindrical antenna stand-off member is provided in the tube sidewall opposite the eye-conforming opening. A fluid tight housing is provided over the bore in the tube. The housing has an opening complementary to the tube bore through which the antenna stand-off member extends in fluid tight relationship. A set screw extends through the housing and permits the antenna section to be translated in height towards or away from the cornea and retained in such position.

Figure 10:
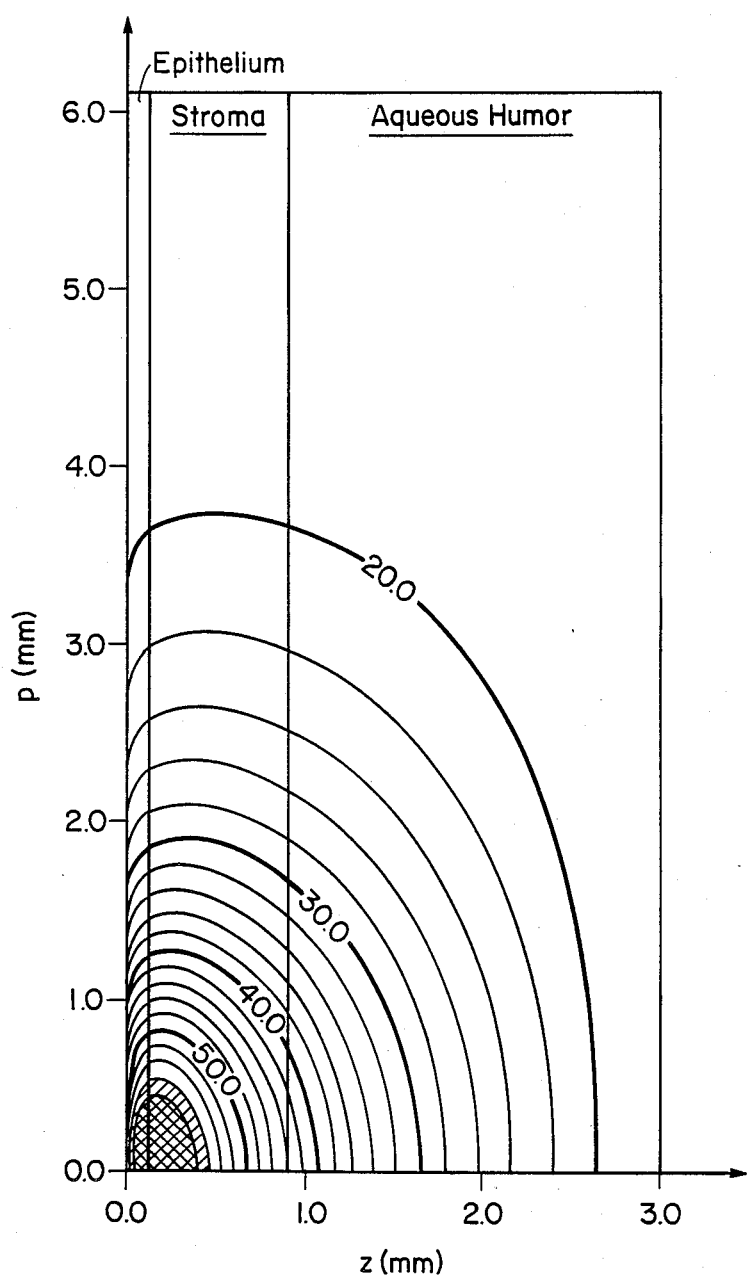
Figure 11:
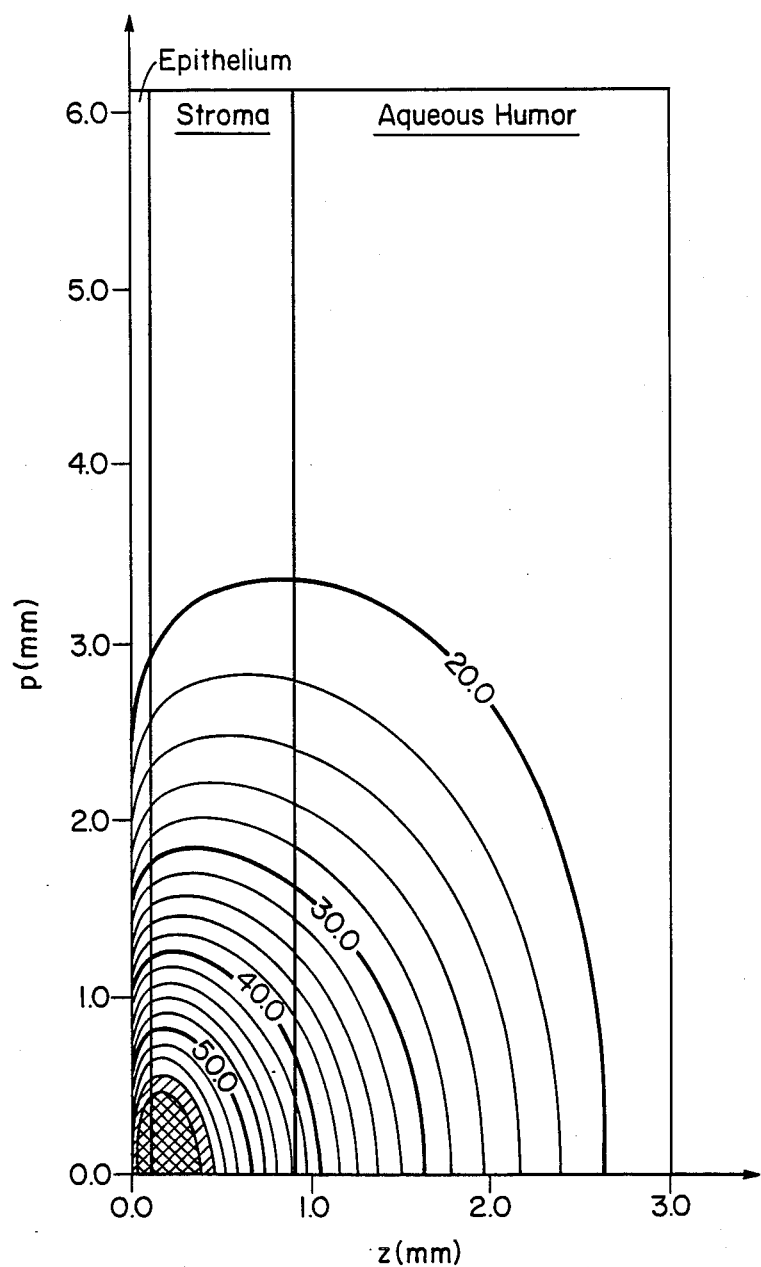

FIG. 10 is a plot of the theoretical iso-temperature lines in the steady-state for radiated power of 2.7 W, 400 mL/min saline flow at 17.5° C., and an antenna-cornea gap 0.67 mm FIG. 11 is a plot of the theoretical iso-temperature lines in the steady-state for radiated power of 2.9 W, 150 mL/min saline flow at 0° C., and an antenna-cornea gap of 0.67 mm.

FIG. 12 is a plot of the theoretical iso-temperature lines in the steady-state for radiated power of 10.7 W, 740 mL/min saline flow at 17.5° C., an antenna-cornea gap of 0.1 mm, and antenna inner conductor OD of 1.37 mm and outer conductor ID of 4.47 mm.

FIG. 13 is a schematic plan view of a hyperopic eye before treatment in accordance with the invention.

FIG. 14 is a schematic cross-section through lines I—I of FIG. 13.

FIG. 15 is a schematic plan view of a hyperopic eye after treatment in accordance with the invention.

FIG. 16 is a schematic cross section through lines II—II of FIG. 15.

DETAILED DESCRIPTION OF THE INVENTION

I. Apparatus Description

Figure 1:
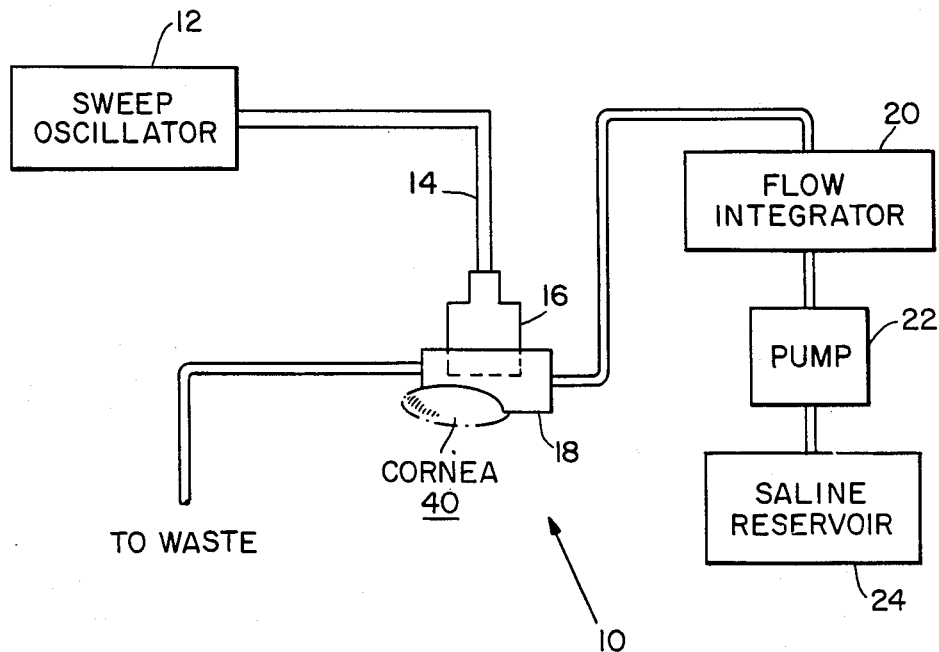
FIG. 1 is a simplified block diagram of the apparatus of the invention.

Based upon experimental and theoretical temperature distributions in the cornea produced by microwave radiation from an open ended coaxial antenna, in combination with surface cooling by forced fluid convection, the applicator system, as shown in FIG. 1, was developed to accomplish simultaneous microwave selective cornea heating at depth, with saline cooling at the cornea surface.

As may be seen in the block diagram of FIG. 1. the system comprises, in general, an electronic portion and a fluid portion. The electronic portion is comprised of a sweep oscillator 12 for generating microwave energy. In the specific embodiment used in the experiments, an oscillator operable at a microwave frequency range of 2-4 gigahertz was employed with a specific frequency of 2450 MHz used since this frequency has previously been safely used in other applications, such as microwave cooking. A frequency range greater than 10 MHz to 10 GHz is contemplated herein to encompass the term "microwave" frequency. A suitable source of microwave energy comprises sweep oscillator 12 which consists of a traveling wave tube amplifier and impedance matching stub tuner. The microwave energy is coupled from sweep oscillator 12 to a coaxial cable 14 to an applicator 10. Applicator 10 is comprised of an antenna section 16 extending in one direction (vertical) and a cooling section 18 extending transverse thereto (horizontal).

The fluid portion is comprised of a saline reservoir 24 in fluid communication with pump 22, which is in turn, fluidly coupled to flow integrator 20 and then to the cooling section 18 of the applicator 10 and, finally, to an outlet conduit leading to a waste disposal receptacle (not shown).

Figure 2:
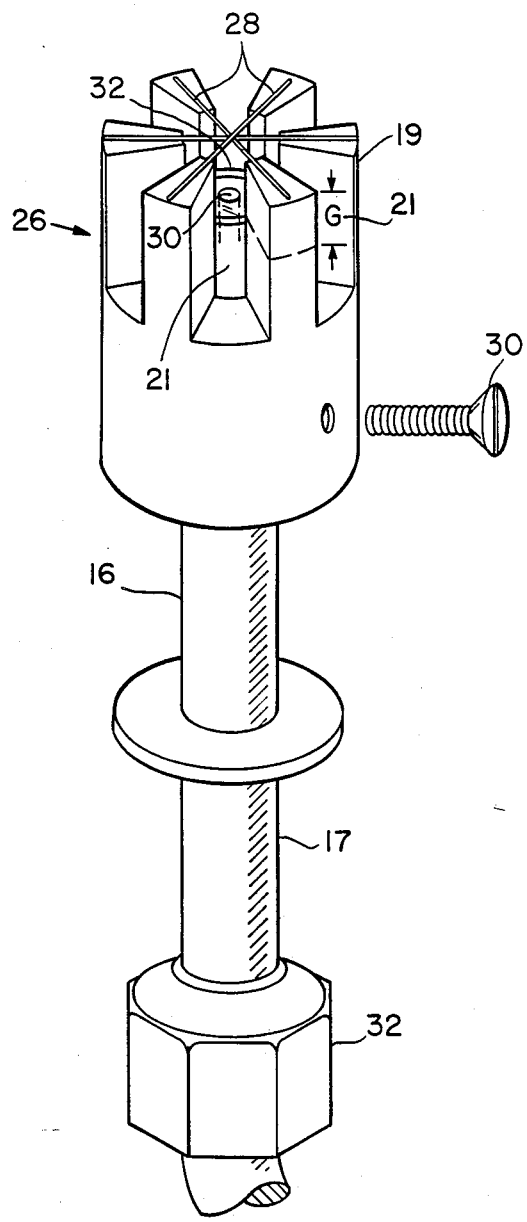
FIG. 2 is an enlarged perspective view of the antenna section of FIG. 1.

The antenna section 16 of the applicator 10 is shown in perspective detail in FIG. 2. The main body of the antenna section 16 is comprised of a longitudinally extending semi-rigid coaxial cable 17. The conductors were separated by a PTFE insulator. In an experimental embodiment, the cable length was 7.5 cm, with inner and outer conductors 30 and 32, respectively, of 0.91 mm OD and 2.98 mm ID, respectively. Connector 32 couples the proximal end of the applicator section 18 to a coaxial cable, which is in turn, coupled to the output of sweep oscillator 12.

At the distal, or applicator end, of antenna section 16, stand-off member 26 is coaxially secured to the cable 17 of the antenna body by set screw 30. The stand-off member is generally cylindrical in shape and is formed of rigid plastic or other suitable material. A longitudinal opening runs from one end to another end of the cylindrical body and through which the coaxial antenna 17 extends and is held in place by set screw 30, leaving a small gap 21 at the distal end between the end of the antenna 17 and the end of the bore in member 26. The member 26 is milled at the distal end to provide wedge shaped stand-off fingers 19, with at least one channel 21 extending between the stand-off fingers transverse to the longitudinal axis of the antenna cable 17. In this manner, as will become apparent from an inspection of FIG. 4, transverse flow of coolant is permitted between the antenna and the cornea through which cooling saline is guided by the channels 21.

Set screw 30 allows the stand-off 26 to be raised or lowered along the axis of the antenna 17 to adjust the gap between the end of the stand-off member 26 and the start of the antenna 17. The cornea 40 (See FIG. 1 or FIG. 4) tends to bulge upwards when the applicator 10 is firmly applied to the eye's surface to form a fluid seal. To prevent this, three plastic threads 28 formed of, for example, nylon, are fixed across the antenna center line at the distal end of the stand-off 26, forming cornea retention means to prevent the cornea from excessive bulging. The threads may be formed of nylon, or similar material, which can be glued to the ends of the fingers 19.

Figure 3:
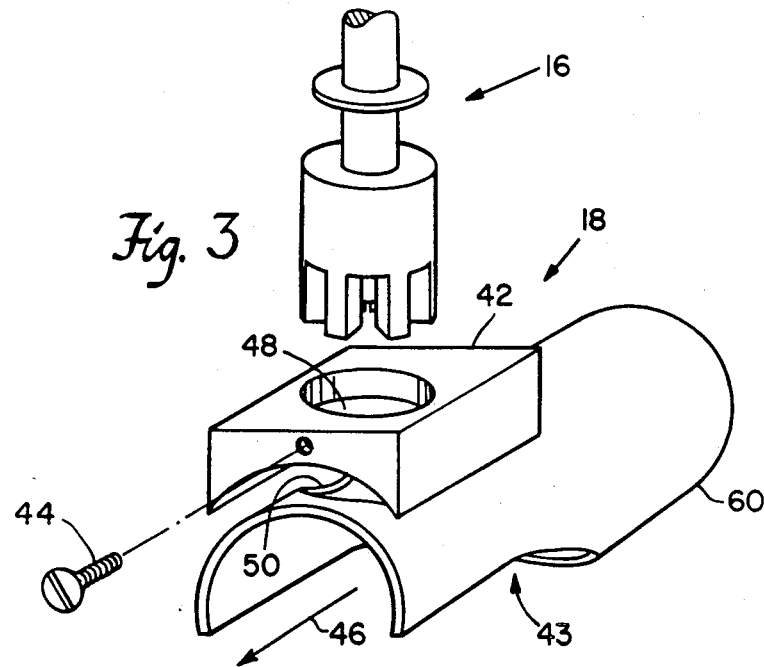
FIG. 3 is an exploded view of the outline section and cooling section 18 of FIG. 1.

As shown in the exploded view of FIG. 3, the cooling section 18 is comprised, in general, of two members; a housing 42 and a curved applicator tube 60. Each may be formed of rigid plastic or other suitable material. One end of the tube 60 is coupled to the pump 22 of FIG. 1 through a flow integrator 20, which smooths out the flow of saline pumped by pump 22 from saline reservoir 24.

The other end of the curved applicator tube 60 is coupled to a waste container (not shown). The applicator tube 60 has an eye-conforming arcuate opening 43 provided in the side-wall of the tube 60. A transverse bore or opening 48 for insertion of the cylindrical antenna stand-off member 26 is provided on the tube opposite the generally eye conforming opening 43.

A housing 42 is provided over the bore 50 in the tube. The housing is glued to the tube 60, providing a substantially fluid-tight covering. The housing serves to stabilize the long antenna 16 in the thin-walled tube 60. The housing 42 has an opening 48 complementary to the tube bore 50 through which the antenna stand-off member extends in substantially fluid-tight relationship. A set screw 44 extends through the housing 42 and permits the antenna section to be translated in height relative to the position of the cornea 40 and retained in such position.

Figure 4:
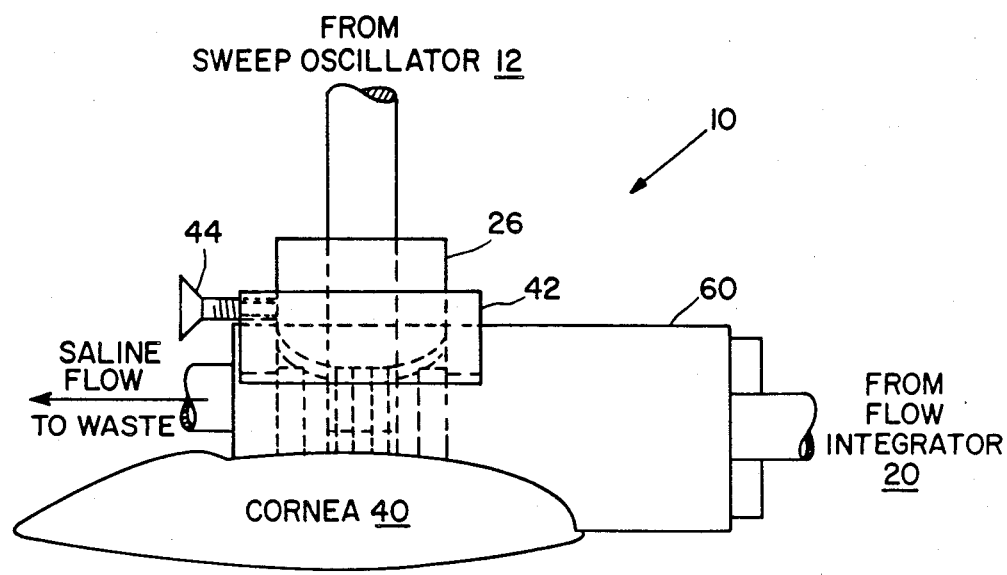
FIG. 4 is a side view of the assembled applicator 10.

FIG. 4 shows the applicator 10 positioned on the cornea 40 and illustrates the relative transverse flow of saline while the microwave radiation is caused to impinge directly on the cornea and penetrate or be absorbed down to a predetermined known depth into the cornea. The amount of radiation absorbed decreases continuously with depth into the tissue. The temperature at the stroma is elevated as the radiation is absorbed. At the same time, the transverse flow of cooling fluid at the surface of the eye prevents the temperature of outer eye tissue, i e., epitheleum, from becoming excessively high In this manner surface heating of the cornea is minimized, while heating of the underlying stroma takes place.

II. Experimental Method

We have heated the corneas of excised steer eyes, in accordance with the invention. Heating was performed within 8 hours of excision. In the interval, the eyes were kept in a sealed, humidified container at room temperature. We first fitted the applicator 10 to the excised eye to make a good fluid tight seal using a ring stand and clamp test fixture to hold the applicator in place on the eye. The saline pump is then turned on and then cw microwave power at 2450 MHz from oscillator 12 is applied for 10 seconds. We found in preliminary studies that a 5 second heating produced little effect, and that 20 seconds was little different from 10 seconds. Afterwards the cornea was excised from the eye, preserved in formalin, stained with hematoxyline and eosin, sliced with 10 micron thickness through the center of the treated spot. mounted in a slide, and photographed. The results were characterized to show the effect on the region of shrinkage of varying saline flow rates, with fixed microwave power and gap size. Preliminary work showed a stand-off gap 21 (See FIG. 2) of about 0.67 mm between the distal end of the antenna 16 and strings 28 was best. A smaller gap impeded the flow of cooling fluid, and a larger gap decreased the microwave power absorbed in the cornea. A microwave source power of 25 W was found to be best in that less power produced little effect, and more power destroyed the epithelium. We made more than 50 heatings in total in this experiment.

Swicord and Davis have derived a theoretical express for the near field of an open-ended coaxial antenna using a magnetic current sheet as the source (M. L. Swicord and C. C. David, "Energy Absorption from Small Radiating Coaxial Probes in Lossy Media", *IEEE Trans. MTT*, Vol. 29, No. 11, Nov. 1981, pp 1202-1209) incorporated herein by reference. We programmed a form of their equations (22) and (23) on a computer and verified the program by computing the near electric field for a case they computed. In our work, the driving frequency was 2450 MHz, giving for cornea tissue a relative permittivity, $\epsilon'$, of 50.4, and a loss tangent, approximately equal to $\epsilon'/\epsilon''$, of 0.343; wherein $\epsilon''$ is the relative loss factor.

In the apparatus of the invention, a layer of cooling fluid is present between the antenna and the cornea surface. We did not model this separate layer electrically, but treated the medium loading the antenna as all cornea. Although saline's relative permittivity is greater than that of cornea (80 vs. 50), we assumed the discontinuity would not affect the fields greatly, since the largest component of electric field near the end of the coaxial cable is parallel to the interface. The loss tangent of saline is close to that of tissue.

Figure 5:
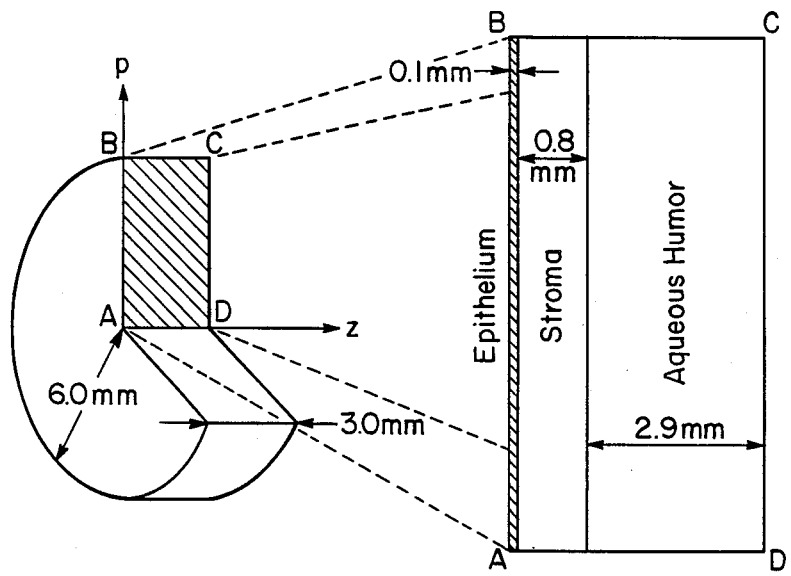
FIG. 5 is a diagram of the cornea and aqueous humour modeled as a two-dimensional axi-symmetric domain for calculation of temperature.
Figure 6:
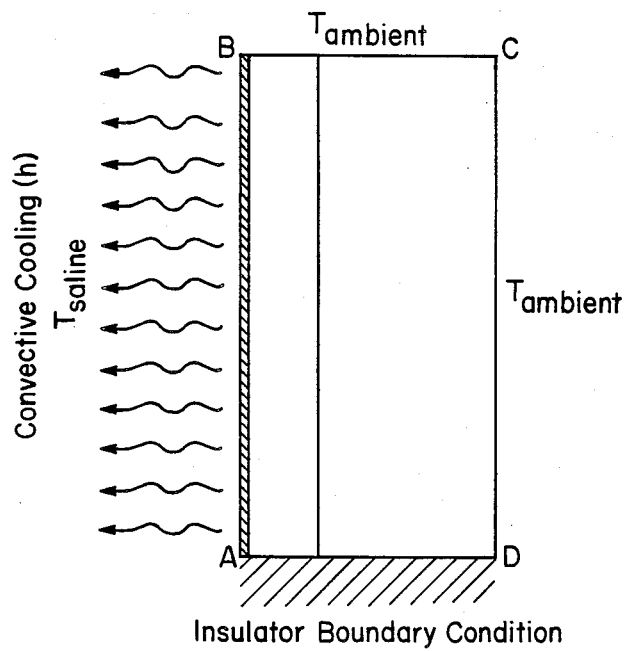
FIG. 6 shows the boundary conditions for calculation of temperature in the eye.

The square of the magnitude of the electric field multiplied by $(\sigma + \omega\epsilon_o\epsilon'')/2\rho$ gives the specific absorption rate (SAR) in W/kg. The quantity $\sigma$ is conductivity, $\omega$ is radian frequency, $\epsilon_o$ is permittivity of a vacuum, and $\rho$ is mass density. This varying function of position forms a distributed heat flux source in the thermal analysis of the problem. We used a finite-element-method heat-transfer analysis program to compute steady-state and transient temperatures on a 2-D axi-symmetric grid representing the cornea and aqueous humour (FIG. 5). We used a domain of 3 mm depth (z axis) and 6 mm width ($\rho$ axis) made up of 600 rectangular elements with a maximum aspect ratio of 6. The boundary conditions were: a fixed temperature equal to ambient at the two edges farthest from the antenna (z=3 mm and $\rho$=6 mm); no heat flux at $\rho$=0, by symmetry; and a known heat flux at z=0 from surface cooling (FIG. 6). The constant temperature boundary condition was 17.5° C., so that results could be compared with experiments conducted on an eye at room temperature.

The surface heat flux is computed from the difference between the known cooling-fluid temperature and the cornea surface temperature, with a thermal resistance determined from the film coefficient of convective heat transfer. This coefficient is approximately computed from the empirical correlation for the Nusselt number for laminar flow over a flat plate. In the geometry of the present invention, the flow is laminar for flow rates less than 700 mL/min. The local Nusselt number is:

$$Nu_x = h_x(x/k) = 0.332 \, Re_x^{\frac{1}{2}} Pr^{\frac{1}{3}},$$

where:

$h_x$ = film coefficient of convective heat transfer at point x(W/m$^2$K), x = distance in m from the beginning of plate to the point of interest (The beginning of the plate is the point of connection between the saline feed tube and the applicator itself), k = thermal conductivity of cooling fluid (W/mK), Pr = Prantl number of fluid at given temperature (dimensionless), $Re_x = vx/\nu$ = Reynold's number at point x (dimensionless).

v = average velocity of fluid (m/sec), and $\nu$ = kinematic viscosity of fluid at given temperature (m$^2$/sec).

Using volumetric flow rate, q(m$^3$/sec), and a cross sectional area for saline flow of 2.69 mm$^2$ with a 0.67 mm antenna.cornea gap, we obtain this relationship between cooling fluid volume flow rate and heat transfer coefficient below the antenna center:

$$h_x = [57.8 \, W/m^2K][(2.44 \times 10^9 \, sec/m^3) \cdot q]^{\frac{1}{2}}$$

Fluid properties were computed at 17.5° C.

As a practical matter, we found that leakage between the cornea and the sides of the applicator became significant at about 800 mL/min. We assume the temperature of the cooling fluid remains constant along the flow path, since a conservative calculation showed the temperature rise is only 0.6° C.

We did not model any variations in thermal properties of the layers of the cornea, because we obtained only averaged values for the cornea as a whole. We measured the thermal conductivity at 0.556 W/m K and thermal diffusivity as $1.45 \times 10^{-7}$ m$^2$/sec. Assuming mass density is 1000 kg/m$^3$, this yields 3830 W/kg K for specific heat. For aqueous humour, we used thermal conductivity =0.578 W/m K and specific heat −4180 J/kg K. We checked for numerical artifacts in the FEM model by making the grid size coarser and by increasing the depth in aqueous humour at which the temperature boundary condition was enforced. A grid with half as many elements yielded a temperature profile with maximum temperature only 0.1 mm deeper. Moving the boundary condition T=0 from z=3 mm to z=6 mm changed the location of the temperature maximum by only 0.007 mm. Thus, we assumed the grid in FIG. 6 was adequate.

We used this theoretical model to predict the effect of varying surface cooling, and compared the results to experiment. We also used the model to predict the heating pattern with a lower cooling-fluid temperature, and a different antenna geometry.

III. Experimental Results

Figure 7:
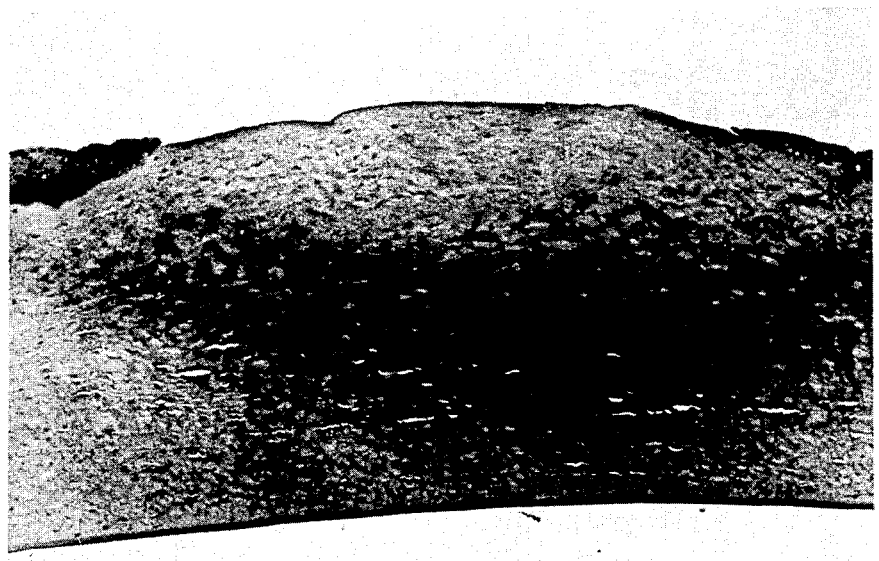
FIG. 7 is a histological cross section of a cornea heated with 25 W source power, 100 mL/min saline flow at 17.5° C., and an antenna-cornea gap of 0.67 mm. (50×mag.)

FIG. 7 (magnification 50×) shows the cross-section of a steer cornea heated with 25 W of microwave source power, a convection coefficient, h, of 3685 S/m$^2$K (flow equals 100 mL/min). and an antenna-cornea gap of 0.67 mm. The epithelium has been lost where heating occurred, and shrinkage extends to 0.65 mm depth, measured from the top of the missing epithelium (thickness 0.15 mm). The length of shrinkage along the surface is 2.4 mm. Note that shrinkage in the direction of the stromal fibers (left-right in FIG. 7) creates a bulging perpendicular to the fiber direction; this identifies the region of shrinkage.

Figure 8:
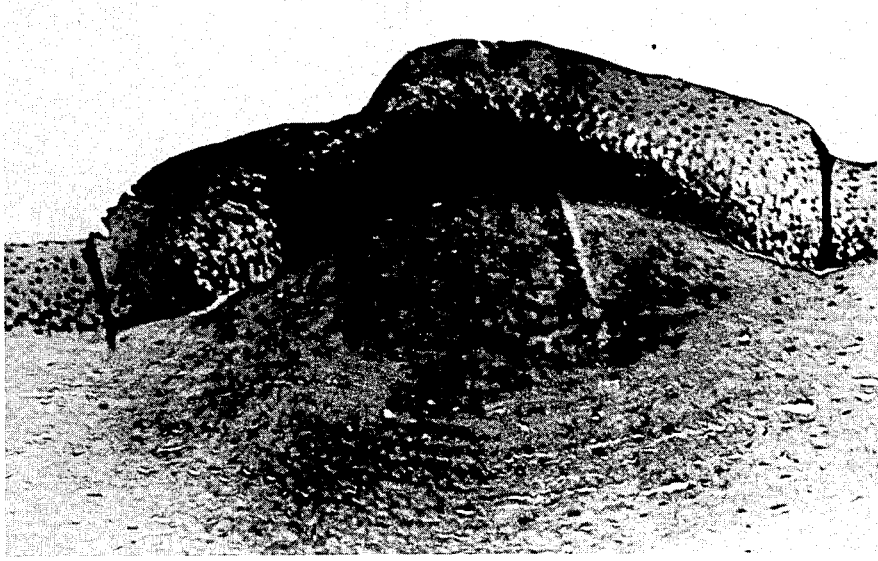
FIG. 8 is a histological cross section of a cornea heated with 25 W source power, 400 mL/min saline flow at 17.5° C., and an antenna-cornea gap of 0.67 mm. (80×mag.)

In FIG. 8 (magnification 80×) all parameters are the same, but the convection coefficient has increased to 7332 W/m$^2$K (flow rate equals 400 mL/min). Here, the epithelium is intact, evidently due to a lower surface temperature. The indentation in the epithelium left of center was caused by the spacing-string 28 of the applicator 10. The two dark, vertical lines in the epithelium near each edge of the photograph, are folds created in the slicing process. Shrinkage extends to 0.59 mm depth, measured from the top of the original epithelium, with a length along the surface of 1.3 mm. (Here, edema has increased the thickness of the epithelium above its normal value of 0.15 mm.) This result is the most favorable one out of about 50 measured with different parameter values. That is. for cases in which the epithelium is intact, the shrinkage region extends deepest.

The termination impedance of the antenna was measured as 16+j22Ω with a saline gap of 0.67 mm; the corresponding power reflection coefficient with a 50Ω line is 0.33.

Figure 9:
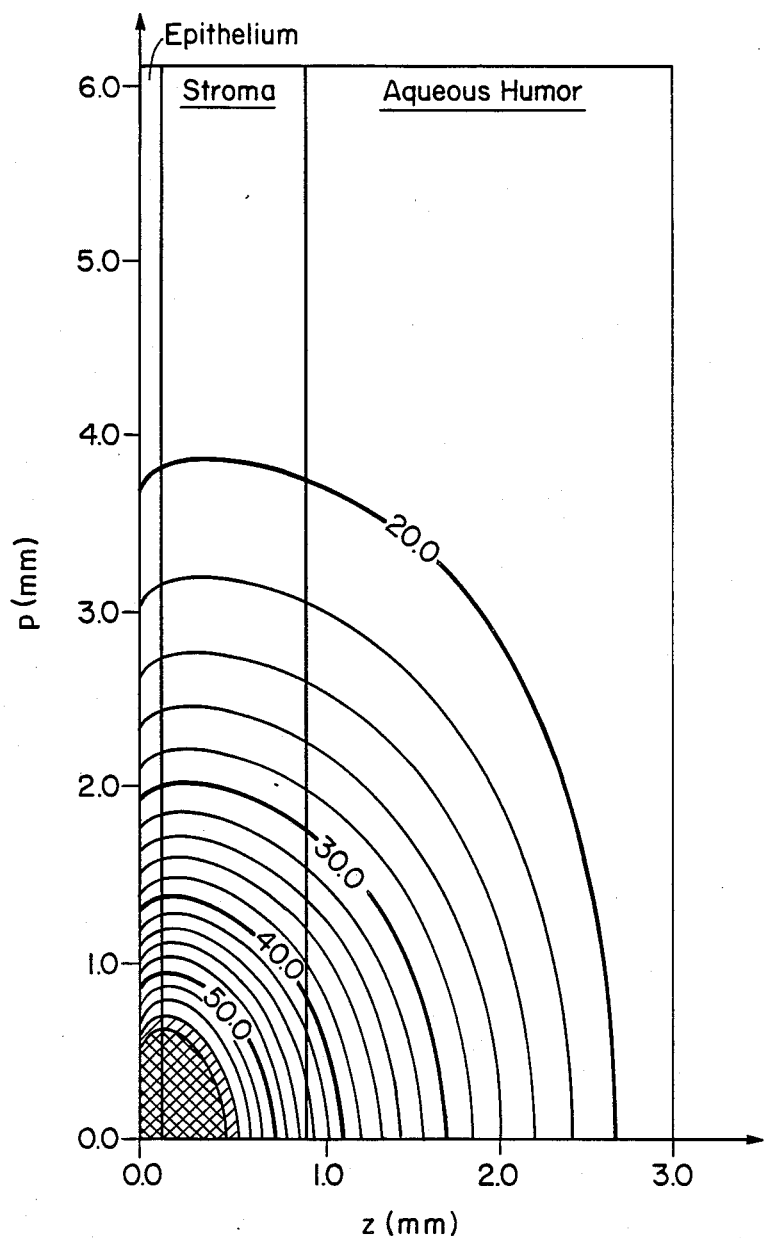
FIG. 9 is a plot of the theoretical iso-temperature lines in the steady-state for radiated power of 1.6 W, 100 mL/min saline flow at 1.75° C., and an antenna.cornea gap of 0.67 mm

FIGS. 9 and 10 show theoretical isotherms in the steady-state for a gap of 0.67 mm and a saline temperature of 17.5° C. In FIG. 9, the surface convection coefficient, h, is 3685 W/m$^2$K (flow rate =100 mL/min), and radiated antenna power is 1.6 W. In FIG. 10, the surface convection coefficient is 7332 W/m$^2$K (flowrate=400 mL/min), and radiated antenna power is 2.7 W Radiated antenna power is the power crossing the plane of the antenna tip into the saline and cornea; it was adjusted to give a 60° C. cornea temperature maximum in all theoretical cases. In the figures, double cross-hatching indicates temperatures between 58° and 60° C.; single cross-hatching indicates temperatures between 56° and 58° C. The smaller convection coefficient in FIG. 9 gives a local maximum 0.2 mm below the cornea surface. The region reaching shrinkage temperature extends to 0.44 mm depth, including the epithelium. The surface temperature is 59° C. at the antenna centerline. The half-width of the region reaching shrinkage temperature is 0.72 mm.

The higher value of convection coefficient in FIG. 10 reduces the region reaching shrinkage temperature. Here, the half-width is about 0.5 mm, and the depth of shrinkage is about 0.44 mm, including the epithelium. The epithelium temperature is reduced to 56° C. on the centerline, but the local maximum remains about 0.2 mm below the cornea surface.

A theoretical calculation of the transient response shows that a temperature within 10% of final value is achieved 10 seconds after a step input of microwave power for the cases above.

FIG. 11 shows steady-state iso-therms for a saline temperature of 0° C., a gap of 0.67 mm, radiated antenna power of 2.9 W, and a convection coefficient of 4487 W/m$^2$K (flowrate=150 mL/min). The surface temperature is 56° C.; the temperature maximum occurs at 0.2 mm depth and shrinkage extends to 0.42 mm depth. This case was not studied experimentally.

In FIG. 12, the antenna outer conductor was increased to 4.47 mm ID, and the inner conductor is increased to 1.37 mm OD; the antenna-cornea gap is 0.1 mm, radiated antenna power is 10.7 W, the convection coefficient is 10,000 W/m$^2$K (flow rate equals 740 mL/min), and the saline temperature is 17.5° C. The maximum temperature occurs beneath the space between inner and outer conductors of the coaxial antenna, not at the antenna centerline. A small antenna-cornea gap was chosen to concentrate power deposition near the outer edge of the antenna. The surface temperature is 50° C. Shrinkage extends to 0.49 mm depth, not including the epithelium. The application for such an antenna is discussed below.

IV. Discussion of Experimental Results

This heating system would not deposit significant power in the ocular lens, since virtually all power is absorbed within a tissue radius equal to the antenna radius. Consequently, as the calculations show, there is no significant temperature rise in the deeper structures. Thus, we would expect no possibility of cataract formation.

The experimental results in FIGS. 7 and 8 indicate that the applicator can produce shrinkage in the stroma, and that a saline flow rate of about 400 mL/min (convection coefficient=7332 W/m$^2$K) is necessary to protect the epithelium. Shrinkage in the central stroma is necessary to produce permanent changes in the shape of the cornea. This apparatus produces shrinkage to a depth of about 0.6 mm from the outside of the epithelium. This does not span the cornea of the steer, which is about 1 mm thick; however, this depth is greater than the thickness of the human cornea, about 0.5 mm. Thus, the endothelium (inner layer) of the human cornea could be heated significantly. Since this is undesirable a smaller diameter antenna scaled to the human cornea should be used to protect the endothelium from a high temperature. The radius in which a fixed fraction of all radiated power is absorbed is directly related to antenna diameter.

With the same parameter values as in the experiment, the theoretical model predicts a local maximum of temperature about 0.2 mm below the epithelium, and predicts a slight reduction in surface temperature when cooling flow rate increases from 3686 W/m$^2$K to 7332 W/m$^2$K. The agreement between theory and experiment is rough, in that shrinkage actually occurs where the maximum temperature is predicted, but the widths and depths of shrinkage are not predicted exactly. The intact epithelium present with the higher cooling rate can be associated with the lower surface temperature predicted under these conditions; evidently, the epithelium may be lost at temperatures around 58° C. It may be that the theory does not predict experiment exactly, due to anisotropic thermal conductivity in the stromal fibers or changes in thermal conductivity after shrinkage. Note that microwave power values differ between theory and experiment due to feedline losses and impedance mismatch.

The experimental and theoretical transient response results agree in that, experimentally. little change in shrinkage was noted between 10 and 20 second heatings, and the steady state was reached in theory in about 10 seconds.

The theoretical model was used to predict the effect of lower saline temperature. This has little effect on the depth of the temperature maximum indicating that it would not be useful to refrigerate the saline.

FIG. 12 indicates that the region of shrinkage will be donut-shaped if the inner conductor is nearly as large as the outer conductor. This idea could be extended so that the inner and outer conductor diameters are comparable to the cornea diameter. In humans, this is about 2 centimeters. Then, shrinkage will occur in a large ring around the cornea center, as shown in the BEFORE and AFTER schematic views of FIGS. 13-16. In the FIGS. 13,14, the eye 60 is shown with an abnormally flat curvature 64; producing hyperopia or too low dioptric lens power. Using an antenna with an inner and outer conductor diameter close to that of the cornea, shrinkage of the stroma will occur in the area between the dotted lines 66 and 68 of FIG. 15 producing circular depressions 72 in the curvature of the eye with consequent bulging in the center 70. Making the cornea center bulge more, should result in a suitable correction for hyperopia.

To protect the endothelium of the thinner human cornea, a larger antenna-cornea gap 21 (See FIG. 2) is recommended, i e., in the order of about 1.0 mm.

In summary, we have found that an applicator constructed in accordance with the invention, is capable of shrinking the stroma of an excised steer cornea as deep as 0.6 mm below the surface. When surface cooling by room temperature saline is enforced, the epithelium remains intact. With this antenna, the region of shrinkage is a small disk about 1 mm across. Antennas of different geometry may be provided in accordance with the invention to shrink the cornea in a pattern suitable for correcting myopia, hyperopia or keratoconus.

Equivalents

This completes the description of the preferred embodiments of the invention. It is to be understood that these embodiments are illustrative of the principals of the invention and that modifications may be implemented by those skilled in the art without departing from the spirit and scope of this invention. For example, the experimental model of the applicator was formed of an easily machinable plastic, such as LEXAN. In commercial embodiments, stainless steel parts may be used.

We claim:

1. An applicator for selectively heating portions of the eye comprising:
   (a) an antenna means for radiating microwave energy in a pattern to apply a portion of said energy at a predetermined depth within the cornea to elevate the temperature of the cornea tissue at said depth to shrink such tissue; and
   (b) cooling means for flowing fluid over the outer surface of the cornea to prevent excessive temperature elevation of the cornea surface tissue during radiation of said microwave energy.

2. The applicator of claim 1 wherein the antenna means has a distal end and a proximal end and comprises a coaxial cable having inner and outer spaced apart conductors coaxial to a central axis and a spacing means is provided coaxial to said cable at the distal end thereof to permit flow of said fluid over said cornea in a path transverse the axis of said cable.

3. The applicator of claim 2 wherein the spacing means is in the form of a member having an opening transverse to the central axis of the coaxial cable.

4. The applicator of claim 3 wherein cornea retention means are provided at a side of the spacing means nearest the distal end of the antenna means for minimizing bulging of the cornea.

5. The applicator of claim 1 wherein the cooling means is comprised of a tubular member having an opening at each end and a sidewall with one end opening being connected to a source of cooling fluid, and a cornea-conforming opening in said sidewall with a circular opening opposite said cornea-conforming opening receiving said antenna means in close proximity with said cornea-conforming opening.

6. The applicator of claim 5 wherein the microwave energy is in the frequency range of from above 10 MHz to about 10 GHz.

7. An applicator for selectively heating portions of the cornea stroma while preventing overheating of the epithelium surface thereof comprising:
   (a) an antenna section having:
     (i) an antenna means in the form of a coaxial cable having a central axis for radiating electromagnetic energy in a predetermined pattern;
     (ii) a stand-off member coaxially secured to said cable at a distal end thereof with channels extending through said member transverse a longitudinal axis thereof; and
   (b) a fluid section having:
     (i) an applicator tube with an opening at each end and a cornea-conforming opening in the side of said tube adjacent one end and a circular opening opposite said cornea-conforming opening receiving said stand-off member therethrough.

8. The applicator of claim 7 further including:
   (a) a housing extending over the circular opening in said tube with an opening therein receiving said stand-off member into said tube in close proximity to said cornea-conforming opening.

9. The applicator of claim 7 wherein said stand-off member is provided with cornea bulge prevention means in the form of cross-members extending transverse the central axis of the cable at an end of the stand-off member adapted to be nearest the cornea.

10. A method for selectively heating portions of the cornea comprising:
   (a) radiating microwave energy in a pattern to produce an elevated temperature level below the cornea surface at a predetermined depth within the cornea;
   (b) while flowing fluid over the outer surface of the cornea to prevent overheating of the cornea surface during radiation of said microwave energy.

11. The method of claim 10 wherein the energy is radiated by an antenna having a central axis, which antenna is in the form of a coaxial cable and the fluid is flowed in a direction transverse the central axis of said antenna.

12. The method of claim 11 wherein an adjustable gap is provided between the end of the antenna nearest the cornea and the cornea surface.

13. The method of claim 12 wherein the adjustable gap is provided by a member having a wedge-shaped opening transverse to the central axis of the antenna.

14. The method of claim 13 including the step of minimizing bulging of the cornea by cornea retaining means at an end of the member nearest the cornea for retaining the cornea.

15. The method of claim 10 wherein the microwave energy is in the range of greater than 10 MHz and less than 10 GHz.

16. A method for selectively heating portions of the cornea while preventing overheating of the surface thereof comprising:
 (a) applying electromagnetic energy to a cornea by radiating said electromagnetic energy in a predetermined pattern from a coaxial cable antenna toward said cornea;
 (b) providing a stand-off member coaxial to said cable at a distal end thereof with channels extending through said member transverse a longitudinal axis thereof and concurrent with applications of said electromagnetic energy cooling the surface of said cornea by circulating fluid through said channels.

* * * * *

UNITED STATES PATENT AND TRADEMARK OFFICE
CERTIFICATE OF CORRECTION

PATENT NO. : 4,881,543
DATED : Nov. 21, 1989
INVENTOR(S) : B. Stuart Trembly and Ralph E. Crump It is certified that error appears in the above—identified patent and that said Letters Patent is hereby corrected as shown below:

First page, Item 73, Assignee: Delete "Massachusetts Institute of Technology, Cambridge, Mass." and insert ---Trustees of Dartmouth College, Hanover, New Hampshire 03756---.

Signed and Sealed this

Sixteenth Day of April, 1991

Attest:

HARRY F. MANBECK, JR.

Attesting Officer

Commissioner of Patents and Trademarks